United States Patent
Ghiasvand et al.

(10) Patent No.: US 10,197,541 B2
(45) Date of Patent: Feb. 5, 2019

(54) COOLING-ASSISTED NEEDLE TRAP DEVICE FOR ANALYZING COMPLEX SOLID SAMPLES USING NANO-SORBENT

(71) Applicants: Alireza Ghiasvand, Khoramabad (IR); Samira Dowlatshah, Khoramabad (IR); Nahid Heidari, Khoramabad (IR)

(72) Inventors: Alireza Ghiasvand, Khoramabad (IR); Samira Dowlatshah, Khoramabad (IR); Nahid Heidari, Khoramabad (IR)

( * ) Notice: Subject to any disclaimer, the term of this patent is extended or adjusted under 35 U.S.C. 154(b) by 267 days.

(21) Appl. No.: 15/083,206

(22) Filed: Mar. 28, 2016

(65) Prior Publication Data

US 2017/0023533 A1    Jan. 26, 2017

(51) Int. Cl.
*G01N 30/12*     (2006.01)
*G01N 1/22*     (2006.01)
*G01N 30/06*     (2006.01)

(52) U.S. Cl.
CPC ....... *G01N 30/12* (2013.01); *G01N 2030/121* (2013.01)

(58) Field of Classification Search
CPC .... G01N 30/12; G01N 2030/121; G01N 1/22; G01N 1/2214; G01N 1/2294; G01N 30/06; G01N 30/54; G01N 30/482; G01N 2030/025; G01N 2030/027; G01N 2030/062; G01N 2030/484; G01N 2030/488; G01N 33/24; G01N 2001/2229
USPC .......... 73/23.35–23.42, 31.07, 61.52–61.61, 73/64.56, 863.12; 210/656–659; 95/82, 95/87, 90–148; 96/101–107, 112, 96/143–146; 422/69, 70, 88, 89
See application file for complete search history.

(56) References Cited

U.S. PATENT DOCUMENTS

| | | | |
|---|---|---|---|
| 4,014,797 A | 3/1977 | Raines | |
| 4,681,301 A | 7/1987 | Rinio | |
| 5,064,418 A | 11/1991 | Cronin | |
| 7,749,443 B2 | 7/2010 | Land, III | |
| 2007/0056360 A1* | 3/2007 | Grant | B01L 3/0275 73/64.56 |
| 2009/0308811 A1* | 12/2009 | Tepper | B01J 20/282 210/656 |
| 2013/0233054 A1 | 9/2013 | Oliphant | |
| 2014/0318274 A1* | 10/2014 | Zimmerman | G01N 30/24 73/863 |

(Continued)

FOREIGN PATENT DOCUMENTS

| | | |
|---|---|---|
| CN | 101397351 A | 1/2009 |
| CN | 101397354 B | 1/2009 |
| CN | 101802084 B | 11/2010 |

(Continued)

*Primary Examiner* — Manish S Shah
*Assistant Examiner* — Suman K Nath
(74) *Attorney, Agent, or Firm* — NovoTechIP International PLLC

(57) ABSTRACT

A cooling-assisted needle trap device for sampling and delivering materials to an analytical device is disclosed. The device includes a needle having a first end and a second end and a side aperture located between the first and second ends. The side aperture provides access to the interior space of the needle. A sorbent is packed within an interior space of the needle between the second end and the side aperture to entrap an analyte within a sample. The cooling-assisted needle trap device also includes a cooling device configured to cool the sorbent.

12 Claims, 5 Drawing Sheets

(56) References Cited

U.S. PATENT DOCUMENTS

2015/0233655 A1\* 8/2015 Ghiasvand ................ F25D 3/10
                                                    165/61
2017/0059533 A1\* 3/2017 Ghiasvand ........... G01N 30/482

FOREIGN PATENT DOCUMENTS

| EP | 2188336 B1 | 5/2010 |
|----|------------|--------|
| MX | 2010002552 A | 5/2010 |
| PT | 2188336 E | 11/2013 |
| SG | 185253 A | 11/2012 |
| WO | 2009036160 A1 | 3/2009 |

\* cited by examiner

COOLING-ASSISTED NEEDLE TRAP DEVICE FOR ANALYZING COMPLEX SOLID SAMPLES USING NANO-SORBENT

CROSS REFERENCE TO RELATED APPLICATION

This application claims the benefit of priority to an Iran Application Serial Number 139450140003000026, filed on Mar. 28, 2015, entitled "A cooling-assisted needle trap device for analyzing complex solid samples using nano-sorbents" and issued as Iran Patent Number 86498 on Aug. 19, 2015, the entire content of which is incorporated herein by reference.

TECHNICAL FIELD

This application relates generally to a cooling-assisted needle trap for sampling that can be used to extract analyte from complicated solid samples and deliver the extracted analyte to a gas chromatography (GC) system. More specifically, the application discloses a cooling system to assist and enhance the extraction of the analyte.

BACKGROUND

Historically, the chief method of analyzing trace volatile chemicals (analytes), was solid-phase micro-extraction (SPME) which employs a fiber to collect the analyte and inject it into a gas chromatograph (GC) or liquid chromatograph (LC). This resulted in the capture and injection of only small quantities of the analytes and thus yielded poor sensitivity. It was discovered that if large quantities of vapor or liquid analyte were drawn through a treated sorbent, the components of interest would be concentrated. Solvents were used to selectively remove the analyte from the sorbent and a small portion of the solvent containing the analytes was then injected into the GC or LC. Concentration of the sample via a sorbent was an improvement in sensitivity over straight analyte injection, but it added many processing steps to the analysis, which could increase errors.

Moreover, the environmental impact, chemical composition, concentration trends, and health effects of airborne particulate matter have been extensively studied and described in the literature. Current sampling methods involve the use of gravimetric filters or impact devices, and a wide variety of light and laser scattering devices. Many of the analytical methods for determination of chemical composition of airborne particulate matter require either sophisticated equipment and/or use strict sample preparation techniques. The task of sampling and analysis of airborne particulate matter is often complicated by the complexity of particle size, particle interactions, chemical partitioning between gaseous and particulate phase, and interactions with the sampling media. The health effects of inhaled particulate matter are associated with both the size and shape, as well as chemical toxicity. One of the better known groups of analytes from the latter category is polycyclic aromatic hydrocarbons.

Amongst pollutants, Polycyclic aromatic hydrocarbons (PAHs) have received increased attention in recent years due to their suspected carcinogenic and/or mutagenic nature. PAHs originate in incomplete combustion, and are commonly found in gasoline and diesel motor exhaust, as by-products of open fires, industrial smoke, cigarette and cigar tobacco and smoke. Other sources include coal tar, coal tar pitch, wood preserving agents and coatings, mineral oils, and asphalt. Current most widely used sampling method, solid phase extraction (SPE), for PAHs involve the use of high-volume pumps, filters and sorbent cartridges. These methods require extraction from a filter (or sorbent) with an appropriate solvent, followed by subsequent analysis by HPLC with fluorescence or UV detection, or gas chromatography/mass spectrometry (GC/MS). Many of these methods require considerable sampling expertise and sophisticated sampling equipment, long sample collection and sample preparation time, and strict extraction procedures. Thus, there is a growing demand for faster, simpler and cost-effective sampling for analytical methods for airborne PAHs without compromising low detection limits achievable with some of the conventional methods. In addition, these new techniques should be reusable and environmentally friendly.

SUMMARY

In one general aspect, the instant application describes a cooling-assisted needle trap device for sampling and sample introduction to an analytical device such as a GC or a LC. The cooling-assisted needle trap device includes a packed needle by a nano-sorbent, having a syringe tip and a working tip, and a side aperture located between the free end and the working tip, next to packed sorbent. The syringe tip is connected to a syringe and the working tip is configured to be inserted into the sample headspace and the headspace flow through the sorbent.

The above general aspect may include one or more of the following features. A sorbent may be packed and placed between the working tip and the side aperture and may be configured to entrap the analyte within the sample received within the interior space of the needle.

A cooling device may be configured to cover and cool the sorbent. The cooling device may include two concentric tubes. The outer tube may have a diameter larger than the inner tube and may include two side holes. The first side hole on the outer tube may be connected to a first capillary tube. The second side hole on the outer tube may be connected to a second capillary tube. The first capillary tube may be configured to be an inlet channel for a coolant fluid. The second capillary tube may be configured to be an outlet channel for the coolant fluid. The inner tube and the outer tube may be equal in length. The first side hole may be positioned near one end of the outer tube. The second side hole may be positioned near the other end of the outer tube. The first capillary tube coupled to the first side hole may have a larger diameter than the second capillary tube coupled to the second side hole to enhance the efficiency of the cooling device.

The cooling-assisted needle trap device may further include a fluid tank connected to the first capillary tube to store the coolant fluid. The cooling-assisted needle trap device may further include a solenoid valve coupled to the first capillary tube on a pathway of the coolant fluid from the fluid tank to the inner tube to control a flow of the coolant fluid flow. A thermocouple may also be connected to the outer concentric tube to measure the temperature inside the cooling device. The needle trap device may be inserted inside an extraction vial. The extraction vial may hold the sample and a heating device may be placed below the extraction vial to heat the sample and thereby increase the releasing of the analyte from the sample.

In accordance with the present application, a syringe may be connected to the free end of the needle trap device to suck the headspace form the interior space of the needle and then return the headspace to the extraction vial for further extraction. The needle made of stainless steel. The sorbent may be mixture of graphene-oxide and silica nano-composite.

The additional details of the present application are set forth in the accompanying drawings and the description below. Once the details of the application are known, additional alternatives and changes will become obvious to one skilled in the art.

BRIEF DESCRIPTION OF THE DRAWINGS

Features of the subject technology are set forth in the appended claims. However, for purpose of explanation, several implementations of the subject technology are set forth in the following figures.

DETAILED DESCRIPTION

Figure 1:
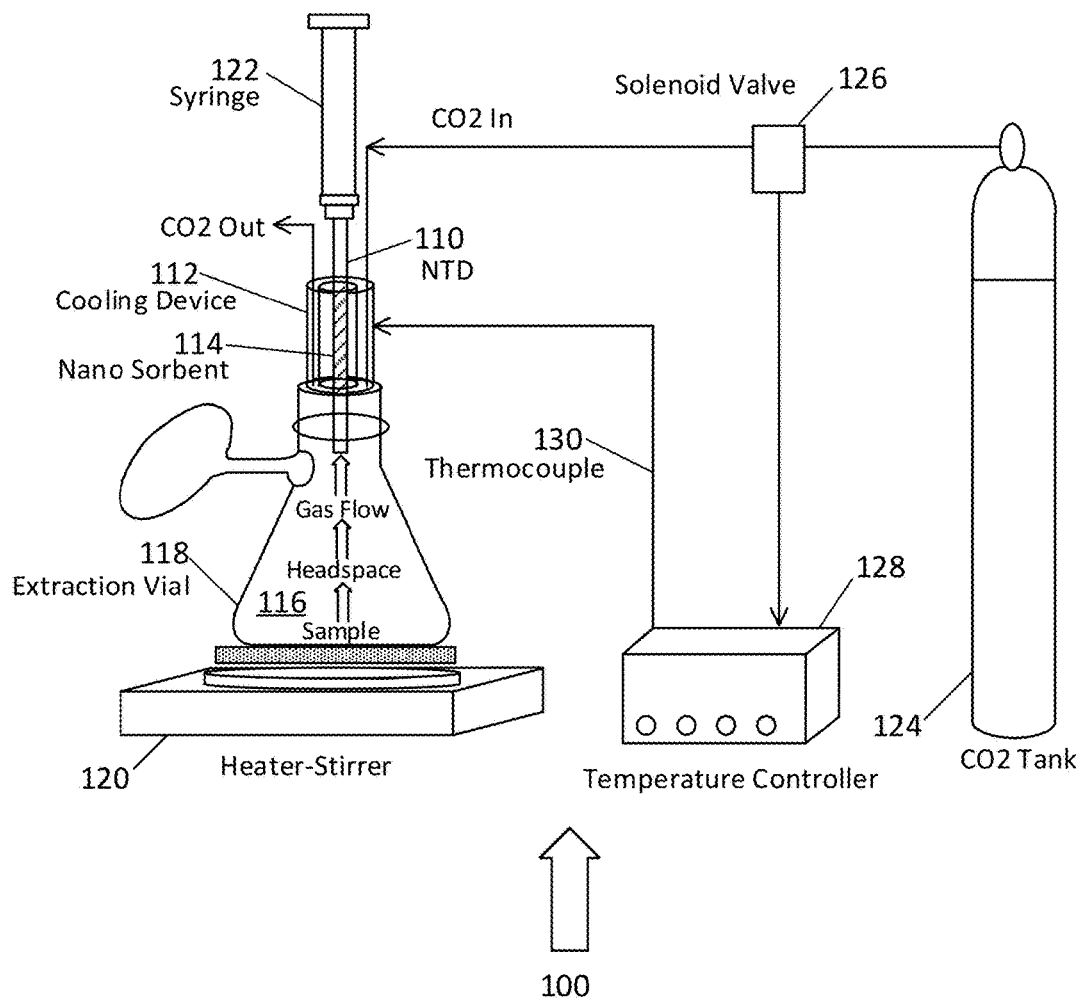
FIG. 1 illustrates a schematic of cooling-assisted needle trap system according to one implementation of the instant application.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The instant application describes a cooling-assisted needle trap system configured to sample and deliver analyte to an analytical device e.g. gas chromatograph, liquid chromatograph. Stainless steel needles, may sized similarly to gas chromatographic injection needles and packed with a sorbent bed, are used for extraction of samples, followed by thermal desorption into GC systems. All analytes, both freely dissolved in the headspace gas and associated with particulate matter entrained in the sample, may be extracted by the devices.

In one implementation, the sorbent is packed into the needle between the working tip and a side hole. For desorption, the needle is inserted into the hot injector of gas chromatograph with a narrow-neck liner. The syringe tip seals against the carrier gas, however, the carrier gas is diverted into the needle through the side hole, subsequently passing through the sorbent, and analytes are thermally desorbed and carried into the GC column. Needle trap device may be used for either spot (grab) sampling or integrated (time-weighted-average sampling. For spot sampling a gas tight syringe or gas sampling pump may be connected to the free end of the needle and used to draw a pre-defined sample volume through the needle. The gas concentration is determined by determining the amount desorbed and dividing by the sample volume.

For integrated sampling, the syringe tip and side-hole are sealed and the open working tip of the needle is exposed to the sample for an extended period of time. The open working tip of the needle provides a suitable diffusion restriction to provide for analyte uptake rates proportional to sample concentration for several hours. The amount desorbed is thus related to the average sample concentration during the entire exposure time.

As for other gas sampling sorbent tubes, sampling rate and volume should be standardized and minimum breakthrough volume should be determined for the target sample during method development. Instrumentation to facilitate automated processing of needle trap device is commercially available for both desorption of multiple field-sampled needle trap device and automated extraction and desorption from sample vials. Automated processing also simplifies method development and the workstation is compatible with a variety of gas chromatographic instruments.

The needle trap device (NTD) may be more robust than solid-phase micro-extraction (SPME). The NTD may also be an efficient particle filter and may have a higher sorbent capacity, which makes it capable of performing exhaustive extraction. Depending on the degree of particle loading in the sample, the devices may be re-used from a few to dozens of times. To date NTD has been used primarily for environmental analysis and breath analysis but is amenable to application for additional analytical chemistry applications. Sampling from headspace of water or solid samples by NTD is a new and challenging topic in this area.

FIG. 1 illustrates a cooling-assisted needle trap device 100 in accordance with one implementation of the instant application. The cooling-assisted needle trap device 100 may include an NTD 110, a cooling system 112, a nano sorbent 114, a sample 116, an extraction vial 118, a heater-stirrer 120, a syringe 122, a fluid tank 124, a solenoid valve 126, a temperature controller 128 and a thermocouple 130.

The NTD 110 includes a first end and a second end. The first end, the syringe tip or the free end, may be configured to engage with a syringe 122 and the second end, the working tip, is configured to be inserted inside an extraction vial 118. The working tip may include an opening for receiving the sample 116 within the body of the NTD 110. The NTD 110 may be covered by the cooling device 112 on the working tip, of the NTD 110.

The cooling system 112 may be located on the lower side of the needle trap device 110, covers a part of the needle trap device 110. The cooling system 112 which is packed by nano-sorbent 114. The cooling system 112 nano-sorbent 114 includes two concentric copper tubes with equal length and different diameters. One of the tubes is placed within the other. The concentric tubes thereby make a jacket with a hollow cylindrical space between the tubes that provides the path for the coolant fluid. In order for the coolant fluid to enter and exit the cooling device 112 which includes the cylindrical hollow space between the concentric tubes, there are two side holes on the outer tube. The cooling process takes place between the concentric tubes. The coolant enters the first hole, flows on the surface of the inner tube and cools down the sorbent which is covered by the inner tube. The first side hole, near one end of the outer tube, is attached to a capillary tube and used as the inlet channel for the coolant fluid. Another side hole on the outer tube, and near the other end of the outer tube, is attached to another capillary tube as the outlet channel for the coolant fluid. A fluid tank 124 is attached to the cooling system to store the coolant fluid. A thermocouple 130 is attached to the outside of the outer concentric tube and coupled to the temperature controller 128. The thermocouple 130 measures the temperature inside the cooling device 112 and sends it to the temperature controller 128. The temperature controller 128 controls the coolant fluid flow through the solenoid valve 126. The cooling device 112 covers the sorbent 114 which is located inside the working tip of the NTD 110. The sorbent 114 adsorbs the analyte from the sample 116.

The sample 116 is placed in an extraction vial 118. In the extraction vial 118 the sample 116 will be heated by a heater-stirrer 120 to enhance the extraction of the analyte. The extracted analyte then enters the working tip of the needle trap device 110, where it is adsorbed by the nano-sorbent 114. Since adsorption of the analyte to the surface of the nano-sorbent 114 is exothermic in nature, the nano-sorbent 114 section of the needle trap device 110 may be cooled by the cooling system 112 to enhance the efficiency of the adsorption process. A syringe 122 attached to the syringe tip of the needle trap device 110 may be used for suction the headspace and then return sample in the headspace to the extraction vial 118. This may be accomplished by removing the syringe 122 from the free end of the needle trap device 110 and inserting it into the extraction vial 118 to repeat the extraction process. The extraction process is assisted by cooling down the nano-sorbent 114 temperature to increase the adsorption capacity of the nano-sorbent 114 via a cooling system 112.

Figure 2:
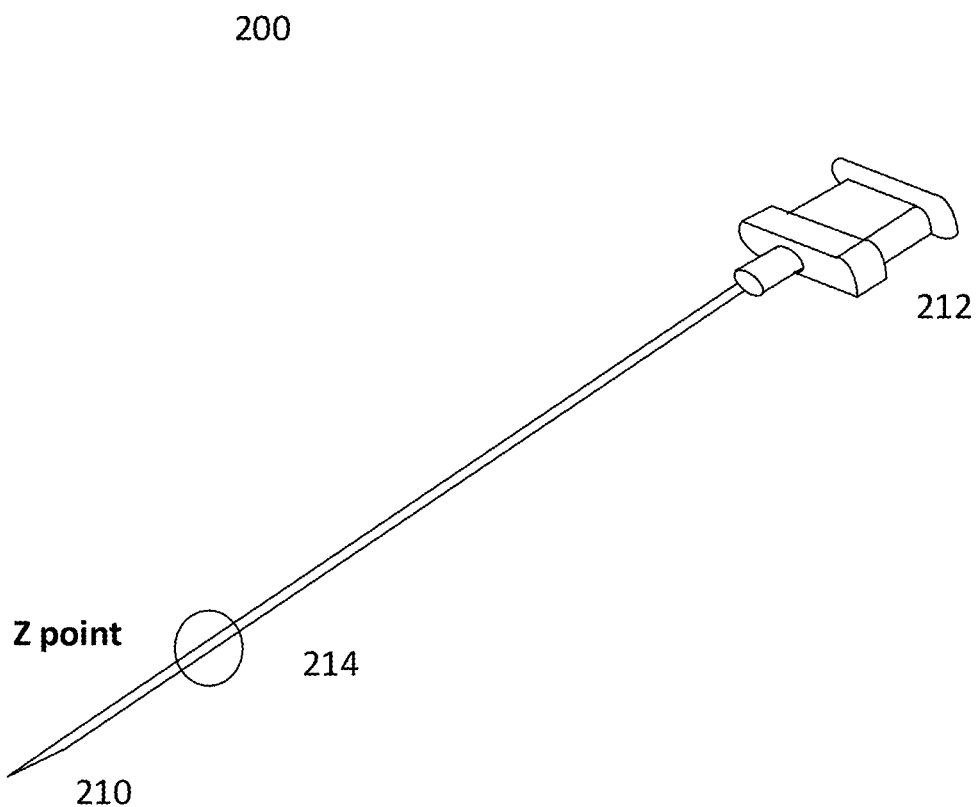
FIG. 2 illustrates an exemplary needle trap device according to one implementation of the instant application.

FIG. 2 illustrates an exemplary NTD 200. The NTD 200 includes a working tip 210, a syringe tip 212, a side hole (side aperture) 214, and a sorbent bed (not shown) positioned inside the NTD 200 between the working end 210 and the side hole 214. The working tip 210 of the NTD 200 surrounded by the cooling system is positioned inside an extraction vial. Upon heating the sample by the heater-stirrer below the extraction vial, the analyte releases from the sample and enters the working end of the needle 200 where it adsorbs on the nano-sorbent surface. The un-adsorbed part of the analyte will be sucked by the syringe and be returned to the extraction vial for further extraction. Unlike the conventional methods where some sample preparation step is required to extract the analytes, the needle trap device is introduced into a conventional GC injector for sample desorption without further preparation steps. The advantages of such a system are many, e.g., the extraction trap device may not require pumps, there may be no solvents involved, the total sampling and analysis time may be relatively short and significantly reduced when compared to many existing methods. As such, it can serve as a screening tool, wherever fast analysis is needed. In addition, such a device can also serve as a time-weighted average sampler, where either continuous sampling over long sampling time or a sequence of short sampling events within a required sampling period is used.

The NTD may include 105 mm long, gauge 21 stainless-steel needle with a side hole packed with graphene-oxide/silica nano-composite, packing nano-composite. The graphene-oxide was synthesized via a modified Hummers' method by using sulfuric acid/potassium permanganate and graphite powder. Afterwards, silica was added to the graphene-oxide by tetraethoxysilane. The synthesized nano-sorbent then packed into the needle. To avoid losing the sorbent while operating, the needle was heat-treated in an oven for 2 hours at 250° C.

Figure 3A:
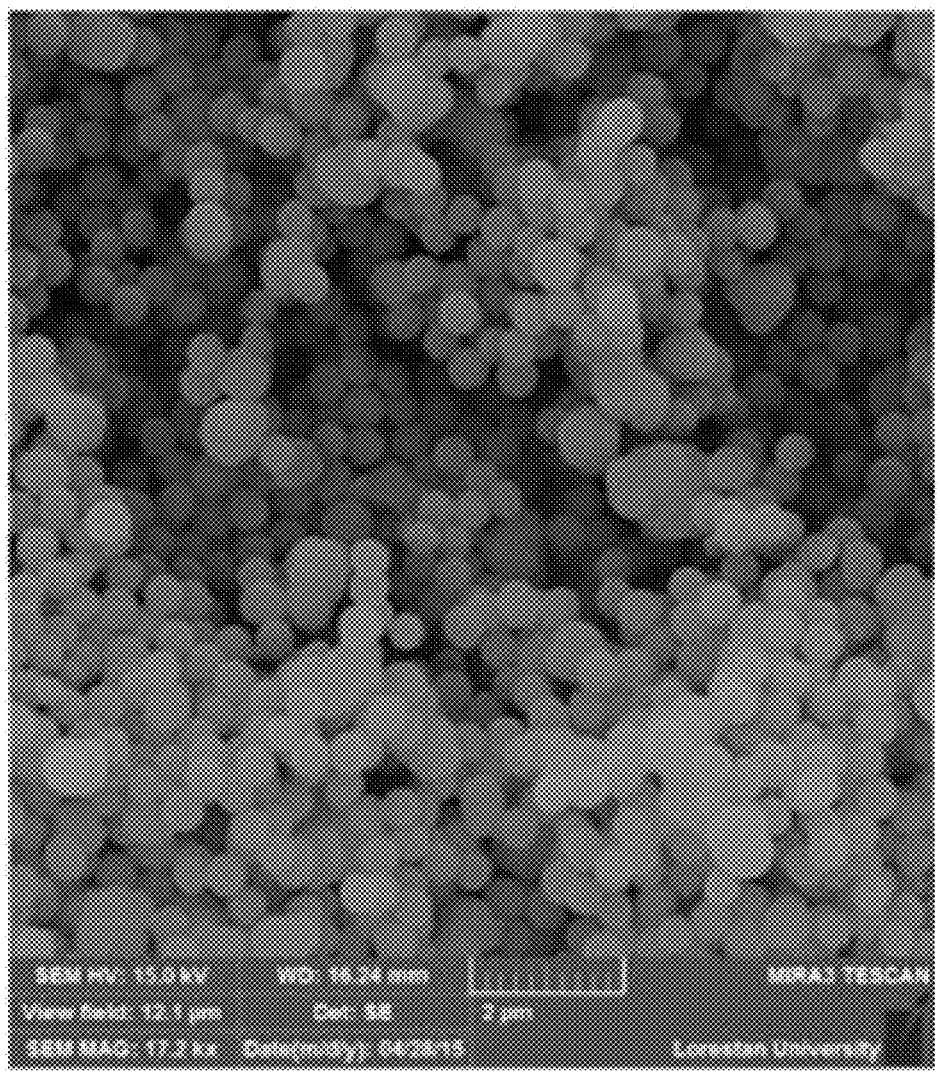
FIGS. 3A and 3B illustrate scanning electron microscopy pictures of the graphene-oxide (3A) and silica nanoparticles (3B)
Figure 3B:
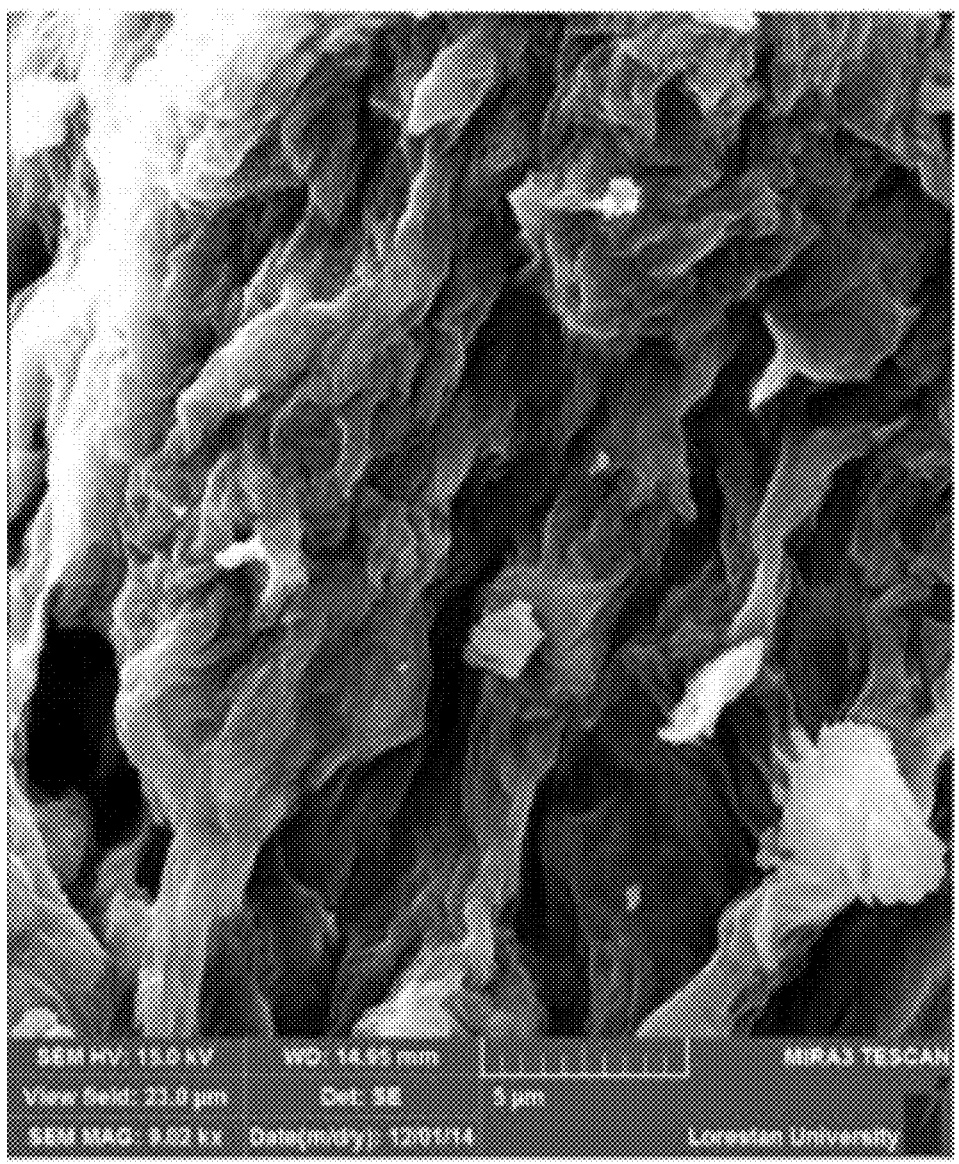
Figure 4:
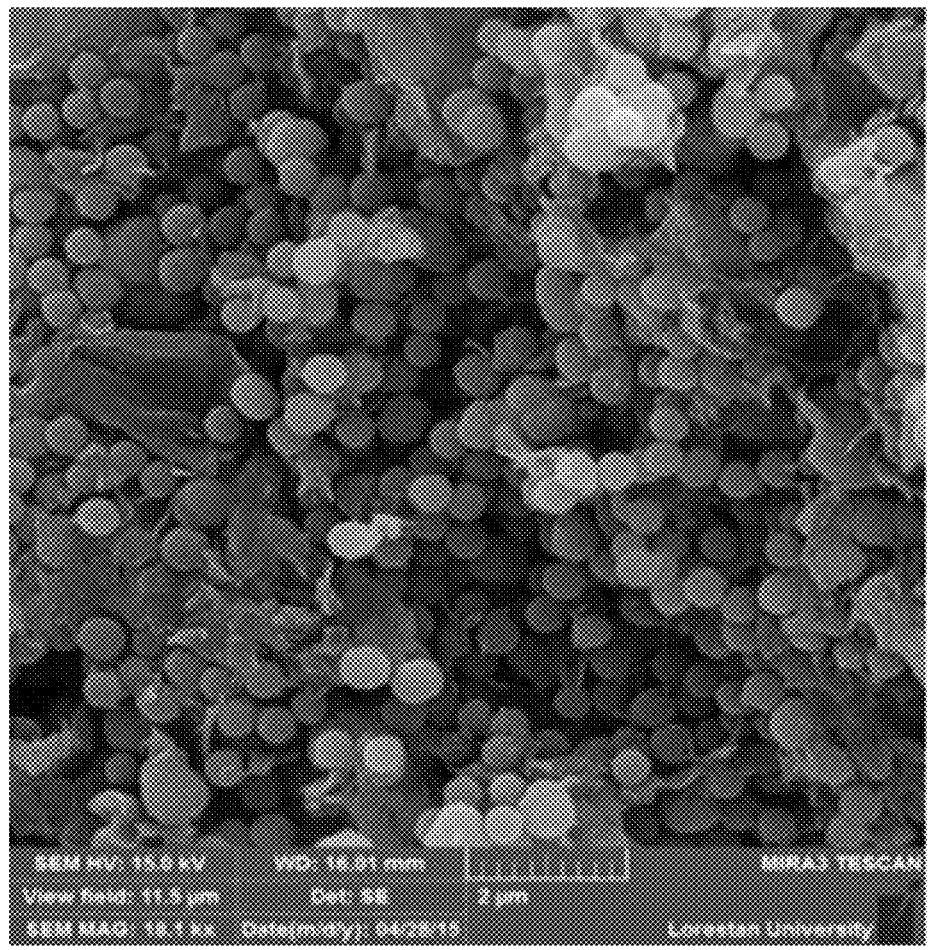
FIG. 4 illustrates a scanning electron microscopy of the graphene-oxide/silica nano-composite.

FIGS. 3A and 3B illustrate scanning electron microscopy images of the synthesized nano-composites. FIG. 3A shows the graphene-oxide nanoparticles and FIG. 3B shows the silica nanoparticles. FIG. 4 also shows the graphene-oxide/silica nano-composites as the sorbent after synthesizing by tetraethoxysilane.

The cooling system may include two concentric copper tubes 2 cm long. The thinner tube may be 0.1 cm in diameter and the thicker tube may be 0.5 cm in diameter. The space between the inner and outer tubes may be used as the pathway for the coolant fluid. Two side holes are drilled near two ends of the outer tube as the inlet and outlet for the coolant fluid. The coolant fluid enters and leaves the concentric tubes by two capillary tubes made of stainless steel. The first capillary tube serves as the coolant fluid inlet, may be 6 cm long and 21-gauge and the second capillary tube which serves as the coolant fluid outlet, may be 4 cm long and 19-gauge. Choosing difference-sized capillary tubes may be for inducing a pressure difference inside the cooling device to enhance the efficiency of the cooling device.

To cool the sorbent, liquid carbon dioxide may be used. A 10 L liquid tank is connected to the cooling device through a solenoid valve which controls the fluid flow. An aluminum-chromium thermocouple attached to the surface of the outer tube of cooling device, measures the temperature of the sorbent and a temperature controller controls the solenoid valve state. When the temperature exceeds a pre-determined threshold, the temperature controller instructs the solenoid valve to open further. The temperature controller closes the solenoid valve when the temperature inside the needle trap device becomes less than a pre-determined threshold.

In one implementation, a syringe may be attached to the free end of the needle trap device to suck the headspace and return the sample within the headspace to the extraction vial while a balloon is attached to the extraction vial in order to inhibit vacuum inside the needle. The balloon may be cleaned properly prior to operation. Moreover, the balloon may become unreactive to the analyte by putting the analyte in contact with the balloon for 24 hours.

In one implementation, after extracting the analyte on the sorbent, the cooling-assisted needle trap device may be detached from the septum and attach to the injection port of a chromatograph e.g. GC-FID to measure the analyte quantitatively. The free end of the needle may be sealed by silicon septum to avoid the carrier gas from purging.

The separation of various components in the examples described above should not be understood as requiring such separation in all examples, and it should be understood that the described components and systems can generally be integrated together in a single packaged into multiple systems.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A cooling-assisted needle trap system comprising:
   a syringe;
   a needle including a first end and a second end and a side aperture positioned between the first end and the second end, the first end being coupled to the syringe, and the side aperture being configured to provide access for carrier gas to enter the interior space of the needle;
   a nano-composite sorbent placed between the second end and the side aperture within the interior space of the needle and configured to entrap an analyte within a sample received within the interior space of the needle, wherein the side aperture is further configured to enable desorption of the entrapped analyte via the carrier gas; and
   a cooling device configured to cover and cool the sorbent and includes an inner tube and an outer tube, the outer tube having a diameter larger than the inner tube and including a first aperture and a second aperture;
   a first capillary tube coupled to the first aperture and configured to be an inlet channel for a coolant fluid for cooling the sorbent; and
   a second capillary tube coupled to the second aperture and configured to be an outlet channel for the coolant fluid;
   an extraction vial configured to hold the sample and receive the second end of the needle from an opening in a top portion of the extraction vial; and
   a heating device placed below the extraction vial and configured to heat the sample, wherein:
   the syringe coupled to the first end of the needle is configured to suck the analyte not adsorbed to the sorbent from the interior space of the needle,
   the analyte not adsorbed to the sorbent is sucked by the syringe from the interior space of the needle and is returned back into the extraction vial and
   the sorbent is graphene-oxide/silica nano-composite.

2. The system of claim 1, wherein:
   the inner tube and the outer tube include substantially equal length,
   the first aperture is included near one end of the outer tube,
   the second aperture is included near another end of the outer tube,
   the first capillary tube coupled to the first aperture has a larger diameter than the second capillary tube coupled to the second aperture to enhance an efficiency of the cooling device, and
   the coolant fluid is configured to enter via the first aperture and circulate an outer surface of the inner tube between the inner tube and the outer tube and exit from the second aperture.

3. The system of claim 1, further comprising:
   a $CO_2$ fluid tank coupled to the first capillary tube and configured to store the coolant fluid;
   a solenoid valve coupled to the first capillary tube on a pathway of the coolant fluid from the fluid tank to the outer tube and configured to control a flow of the coolant fluid flow;
   a thermocouple coupled to the outer tube to measure a temperature of the cooling device; and
   a controller configured to control an operation of the solenoid valve based on the temperature measured by the thermocouple.

4. The system of claim 1, wherein the needle is made of stainless steel.

5. The system of claim 1, wherein the needle is approximately 105 mm long and 21-G in diameter.

6. The system of claim 1, wherein the side aperture is approximately 3 cm from the second end of the needle.

7. The system of claim 1, wherein the sorbent is heat-treated by passing an inert gas through it in an oven for 2 hours at 250° C.

8. The system of claim 1, wherein the inner and outer tubes are made of copper.

9. The system of claim 1, wherein the inner and outer tubes are approximately 2 cm in length, wherein the outer tube is approximately 0.5 cm in diameter and the inner tube is approximately 0.1 cm in diameter.

10. The system of claim 1, wherein the capillary tubes are made of stainless steel, wherein the first capillary tube is approximately 6 cm in length and 21-G in diameter and the second capillary tube is 4 cm in length and 19-G in diameter.

11. The system of claim 1, wherein the coolant fluid is liquid carbon dioxide.

12. The system of claim 3, wherein the thermocouple is Aluminum-Chromium.

* * * * *